(12) United States Patent
Brock-Fisher

(10) Patent No.: US 6,464,643 B1
(45) Date of Patent: Oct. 15, 2002

(54) CONTRAST IMAGING WITH MOTION CORRECTION

(75) Inventor: George A. Brock-Fisher, St Andover, MA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/684,858

(22) Filed: Oct. 6, 2000

(51) Int. Cl.[7] ............................................... A61B 08/00
(52) U.S. Cl. ...................................................... 600/458
(58) Field of Search ................................. 600/440, 441, 600/443, 447, 458, 459, 444, 449, 445, 455

(56) References Cited

U.S. PATENT DOCUMENTS

| 5,456,257 A | * | 10/1995 | Johnson et al. | ............. 600/443 |
| 5,833,613 A | * | 11/1998 | Averkiou et al. | ........... 600/440 |
| 6,186,950 B1 | * | 2/2001 | Averkiou et al. | ........... 600/443 |
| 6,213,951 B1 | * | 4/2001 | Krishnan et al. | ........... 600/458 |
| 6,228,031 B1 | * | 5/2001 | Hwang et al. | ............... 600/447 |

* cited by examiner

Primary Examiner—Francis J. Jaworski
Assistant Examiner—Maulin Patel
(74) Attorney, Agent, or Firm—John Vodopia

(57) ABSTRACT

The present disclosure relates to a method for imaging contrast agents within a patient's body. The method generally comprises, receiving echoed signals from the body, processing the received data to correct for motion effects, processing the received data to suppress tissue response, and imaging the contrast agents.

36 Claims, 5 Drawing Sheets

CONTRAST IMAGING WITH MOTION CORRECTION

FIELD OF THE INVENTION

The present disclosure relates to contrast imaging. More particularly, the present disclosure relates to methods for contrast imaging with which tissue motion is compensated to enhance the sensitivity to contrast agents by reducing motion-related image artifacts.

BACKGROUND OF TITLE INVENTION

The use of ultrasound imaging has grown quickly due to the image quality achievable, its safety, and its low cost. Such imaging can be broken into two general categories: tissue imaging and contrast imaging. In contrast imaging, contrast agents, for example microbubbles of heavy gas encapsulated in rupturable shells of material, are introduced intravenously into the bloodstream. Due to their physical characteristics, contrast agents stand out in ultrasound examinations and therefore can be used as markers that identify the amount of blood flowing to or through the observed tissue. In particular, the contrast agents resonate in the presence of ultrasonic fields producing radial oscillations that can be easily detected and imaged. Normally, this response is imaged at the second harmonic of the transmit frequency $f_0$.

Recently, it has been determined that tissue also produces harmonic responses which influence the images produced during contrast imaging. Several techniques have been developed which take advantage of the primarily linear response behavior of tissue to cancel or attenuate the linear tissue signals. In several of these techniques, multiple transmit lines are fired along the same line of sight into the body. The transmit waveform is modified (e.g., in terms of power, phase, or polarity) from line to line to produce a variation in the response received by the transducer. These data points are then processed to remove the influence of their linear components to yield data that primarily contains the non-linear response of the contrast agents.

Although the above-described techniques work well in removing the influence of stationary tissue, flash artifacts from moving tissue can degrade the resultant images. In particular, this movement causes decorrelation of the received echoes that is not compensated for with typical processing techniques. This degradation can be substantial, particularly where the heart is being imaged due to its frequent and rapid motions. Attempts have been made to reduce the effects of such movement by applying two-zero filters to the responses of the receive signals associated with the various transmit lines. However, this technique assumes perfectly linear tissue movement and therefore is not completely effective in removing the moving tissue signals.

From the above, it can be appreciated that it would be desirable to have a method for contrast imaging in which the response of moving tissue is effectively suppressed so as to enhance the imaging sensitivity of the contrast agents.

SUMMARY OF THE INVENTION

The present disclosure relates to apparatus and methods for imaging contrast agents within a patient's body. The method generally comprises receiving echoed signals from the body, processing the received data to correct for motion effects, processing the received data to suppress tissue response, and imaging the contrast agents.

In a preferred embodiment, the ultrasound signal comprises a plurality of signal lines that have been modulated to have different transmit characteristics. In the preferred embodiment, the step of processing to correct for motion effects comprises measuring the Doppler shift of the received data to generate a motion estimate representative of tissue and contrast agent motion within the body. This motion estimate can then be used to time-correct the received data thereby compensating for motion effects in the received data.

The features and advantages of the invention will become apparent upon reading the following specification, when taken in conjunction with the accompanying drawings.

BRIEF DESCRIPTION OF THE DRAWINGS

The invention can be better understood with reference to the following drawings. The components in the drawings are not necessarily to scale, emphasis instead being placed upon clearly illustrating the principles of the present invention.

DETAILED DESCRIPTION

The present disclosure generally relates to contrast imaging. According to one aspect of the invention, contrast agent detection techniques are used to image contrast agent concentrations in certain areas of human tissue. In another aspect of the invention, these techniques are used to measure the direction and velocity of contrast agent flow through the bloodstream. In either case, however, motion correction is used to suppress the influence of moving tissue on the signals received from the body. Due to this motion correction, the contrast agents can be more easily and more clearly imaged.

Figure 1:
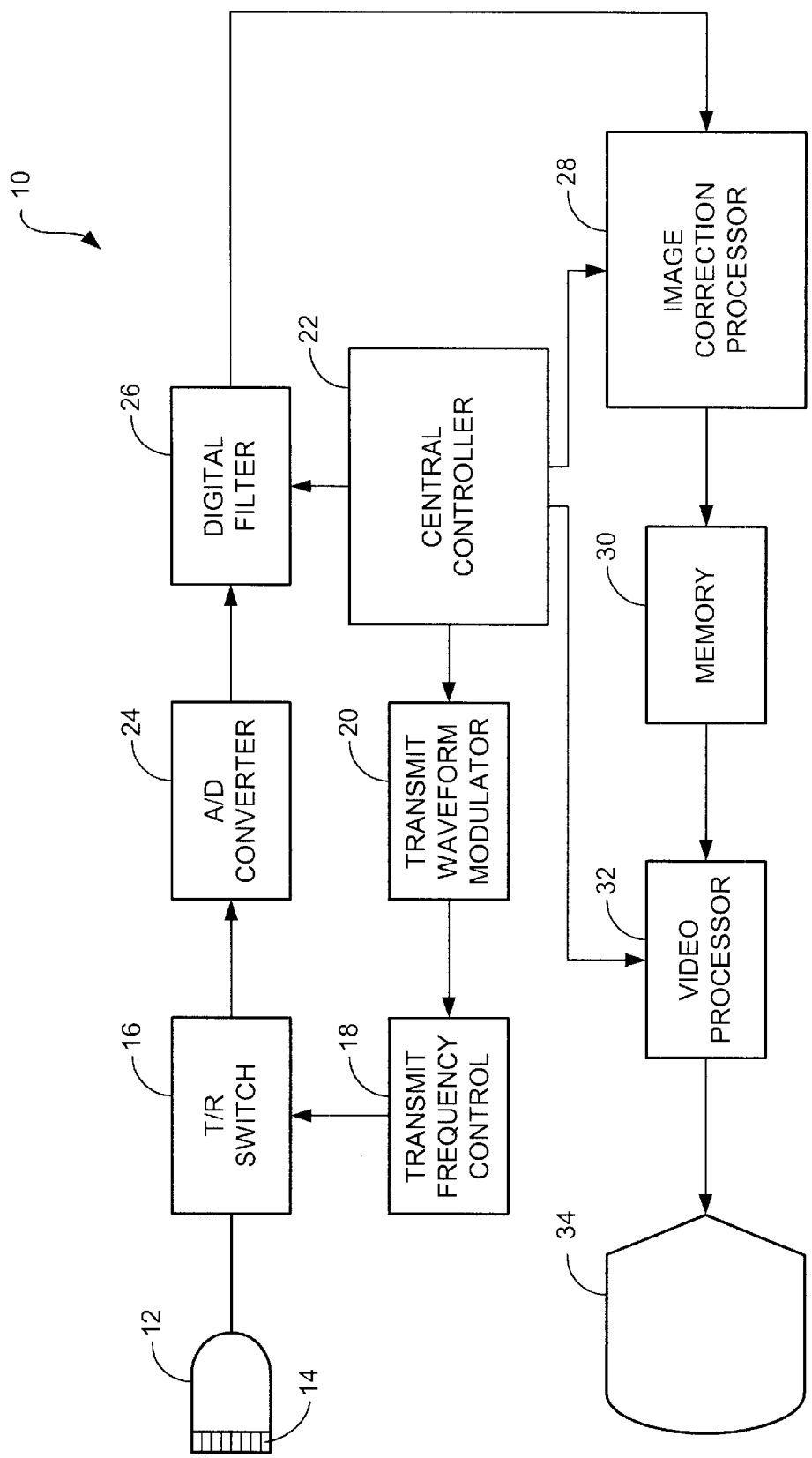
FIG. 1 is a block diagram of a contrast imaging system of the present invention.

Referring now in more detail to the drawings, in which like numerals indicate corresponding parts throughout the several views, FIG. 1 illustrates a contrast imaging system 10 of the present invention. It will be appreciated that this figure does not necessarily illustrate every component of the system, emphasis instead being placed upon the components most relevant to the methods disclosed herein. As indicated in FIG. 1, the system 10 comprises a probe 12 that includes an array transducer 14 that is used to transmit and receive signals. The probe 12 is electrically connected to a T/R switch 16 which places the probe in a transmit or receive mode. On the transmit side, the system 10 includes a transmit frequency control 18 and a transmit waveform modulator 20 that, under the control of a central controller 22, sets the transmit frequency $f_0$ of the transmit signals and modulates the various transmitted signal lines, respectively.

On the receive side, the system 10 includes an A/D converter 24 which converts the analog signals received from the probe 12 into digital signals and a digital filter 26 (e.g., an RF filter) that filters signals outside the desired receive band from the received data. In addition, the receive side includes an image correction processor 28 which records the data for tissue and contrast agent motion effects and suppresses the stationary tissue signal components. The corrected data can be stored in a memory 30 and, after being processed by a video processor 32, displayed on a display device 34.

Figure 2:
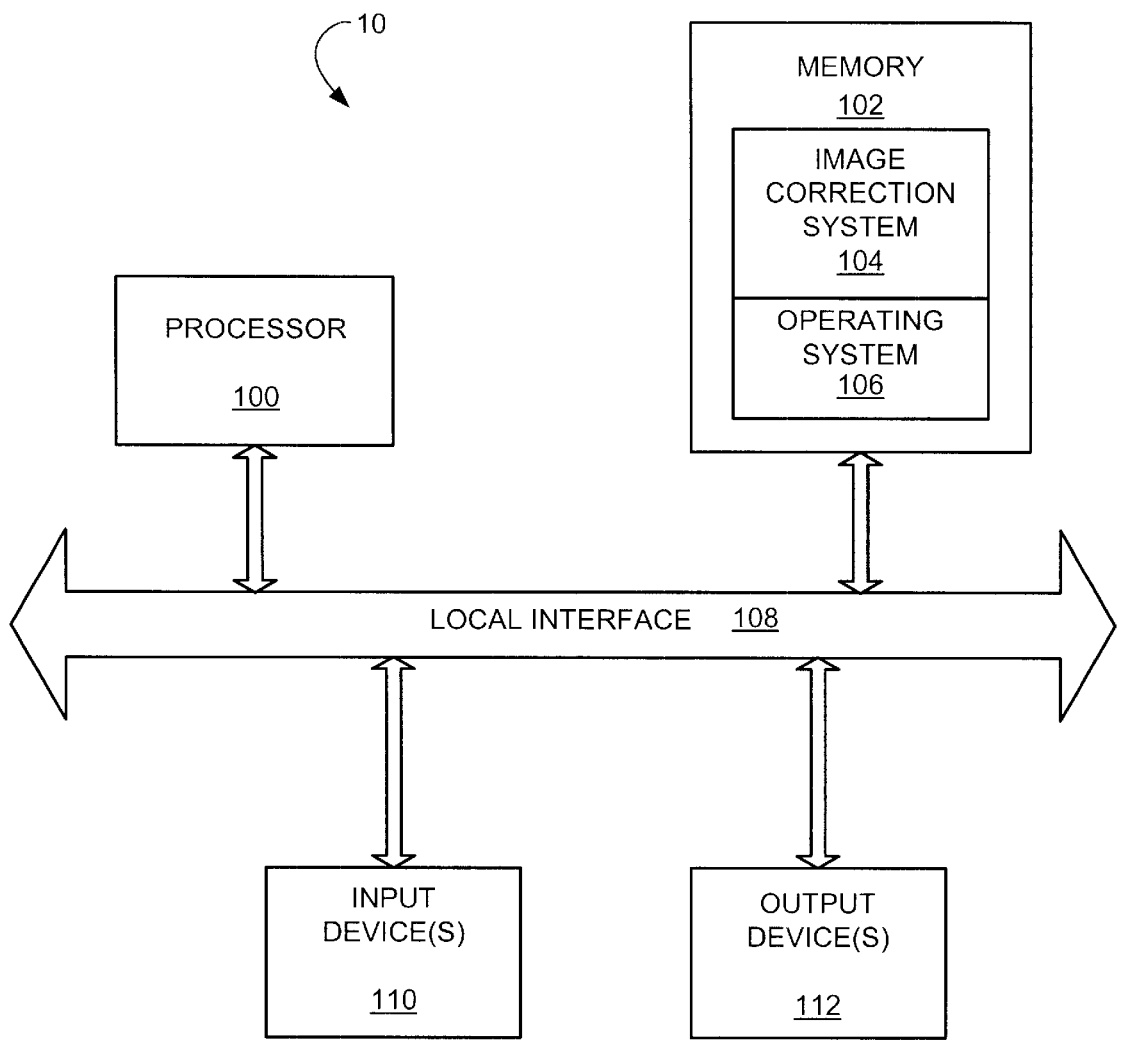
FIG. 2 is a functional block diagram of the system shown in FIG. 1.

FIG. 2 illustrates the functional components of the contrast imaging system 10 shown in FIG. 1. As depicted in FIG. 2, the system 10 typically comprises a processor 100, a memory 102, a local interface 108, and an output device 112. Typically, the memory 102 includes, inter alia, an image correction system 104, as well as an operating system 106. Furthermore, the memory 102 can include the memory 32 shown in FIG. 1. As will be appreciated by those having ordinary skill in the art, the image correction system 104 can be implemented in software, hardware, or a combination thereof within the image correction processor 30 shown in FIG. 1. It is to be noted that when implemented in software, the system 104 can be stored and transported on any computer readable medium for use by or in connection with an instruction execution system, apparatus, or device, such as a computer-based system, processor containing system, or other system that can fetch the instructions from the instruction execution system, apparatus, or device and execute the instructions.

In the context of this disclosure, a "computer readable medium" can be any means that can contain, store, communicate, propagate, or transport the program for use by or in connection with the instruction execution system, apparatus, or device. The computer readable medium can be, for example, an electronic, magnetic, optical, electromagnetic, infrared, or semiconductor system, apparatus, device, or propagation medium. More specific examples of computer readable media include the following: an electrical connection having one or more wires, computer diskette, random access memory (RAM), read only memory (ROM), erasable programmable read only memory (EPROM or Flash memory), an optical fiber, and a compact disk read only memory (CD ROM). It is to be noted that the computer readable medium can even be paper or another suitable medium upon which the program is printed as the program can be electronically captured, via for instance optical scanning of the paper or other medium, then compiled, interpreted, or otherwise processed in a suitable manner if necessary, and then stored in a computer memory.

Figure 3:
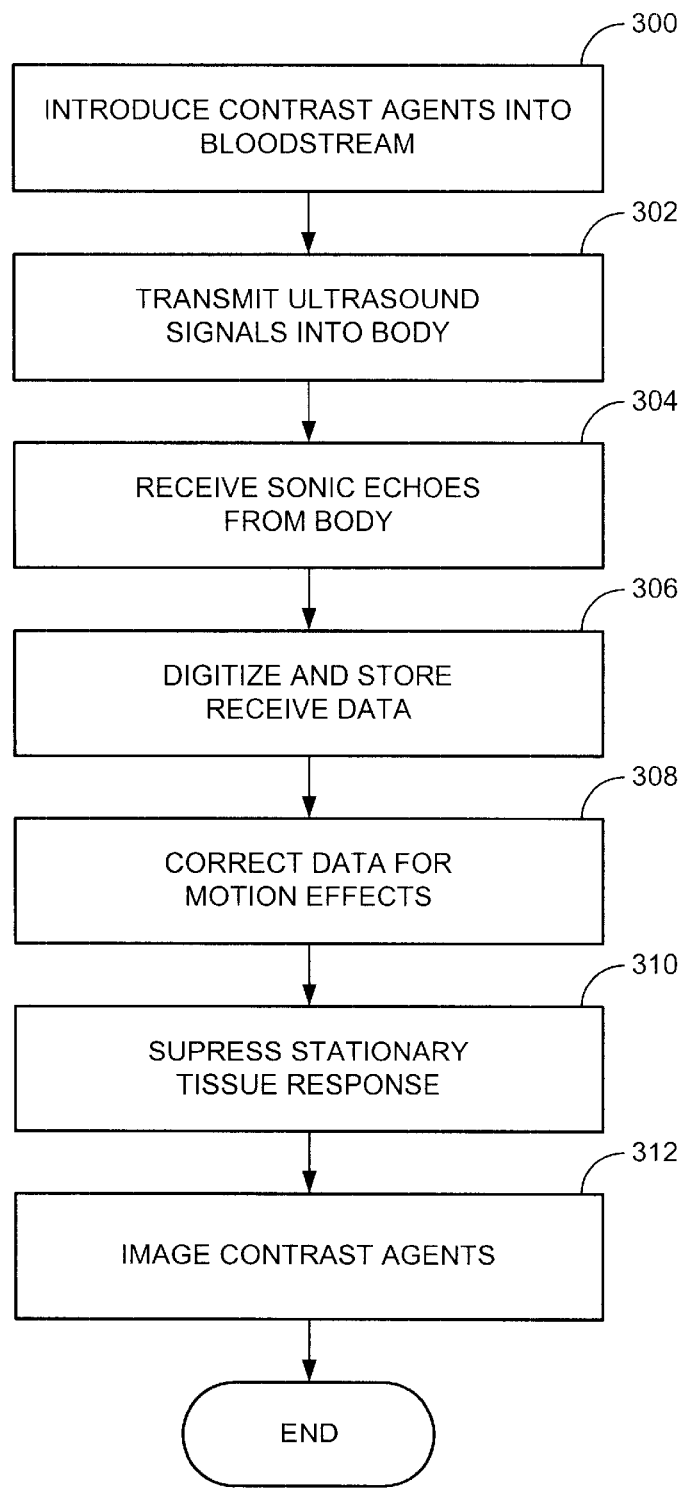
FIG. 3 is a flow diagram of a method for contrast imaging of the present invention.

With reference to FIG. 3, a contrast imaging method of the present invention will be discussed. In particular, FIG. 3 illustrates a high level contrast imaging method and therefore provides a general overview of the inventive method. As indicated in block 300, contrast agents are first introduced intravenously into the patient's bloodstream, These contrast agents can comprise microbubbles of a heavy gas, such as a perfluorocarbon gas encapsulated in an outer shell made of protein, lipid, or other suitable material. Although the size of the agents may vary depending upon the application, these microbubbles normally are in the range of approximately 1.0 to 15 microns ($\mu$m) in diameter. As the contrast agents are introduced into the bloodstream, they travel throughout the cardiovascular system.

After these contrast agents have reached the area to be imaged, ultrasound signals are transmitted into the body, as indicated in block 302. When these acoustic signals intercept the various targets (i.e., tissue and agents) within the body, sonic echoes are produced that can be received by the transducer as indicated in block 304. Where contrast agents are to be imaged, these echoes are normally received at the second harmonic of the transmit signals. Accordingly, the receive frequency typically will be twice that of the transmit frequency $f_0$. As is known in the art, reception of signals at the second harmonic is advantageous in that contrast agents resonate at this frequency to a much greater extent than does human tissue. Accordingly, the response of the contrast agents can be differentiated from human tissue. Despite this difference in response characteristics, human tissue does produce harmonic responses. Accordingly, the signals received from the body of the patient will normally comprise both contrast image components and tissue components.

Once the signals have been received from the body, these signals can be digitized and stored, as indicated in block 306, so that the data contained therein can be processed and ultimately imaged. After the received data has been stored, a first stage of processing is exercised on the data to correct the data for motion effects as indicated in block 308. As is discussed in greater detail below, this processing normally comprises generating a motion estimate for each sample depth along each line. With this motion estimate, the original received data can be processed to remove the effects of moving tissue and contrast agents. As described above, the effects of moving tissue can be substantial, especially when areas near or within the heart are being imaged. Notably, tissue movement can also be created by patient breathing, coughing, or other such movements. Regardless of the source of the movement, however, it is preferable that this movement be compensated for such that flash artifacts that degrade the imaging of the contrast agents are suppressed.

Once the received data has been compensated for the effects of motion, the linear components of the receive data can be removed to suppress the tissue response in a second processing stage, as indicated in block 310. Thereafter, the contrast agents can be imaged using contrast data processing techniques as indicated in block 312. As described below, this imaging can comprise simply imaging the concentration of the contrast agents within human tissue, or can comprise identifying the direction and velocity of flow of contrast agents within the bloodstream or tissues.

Figure 4:
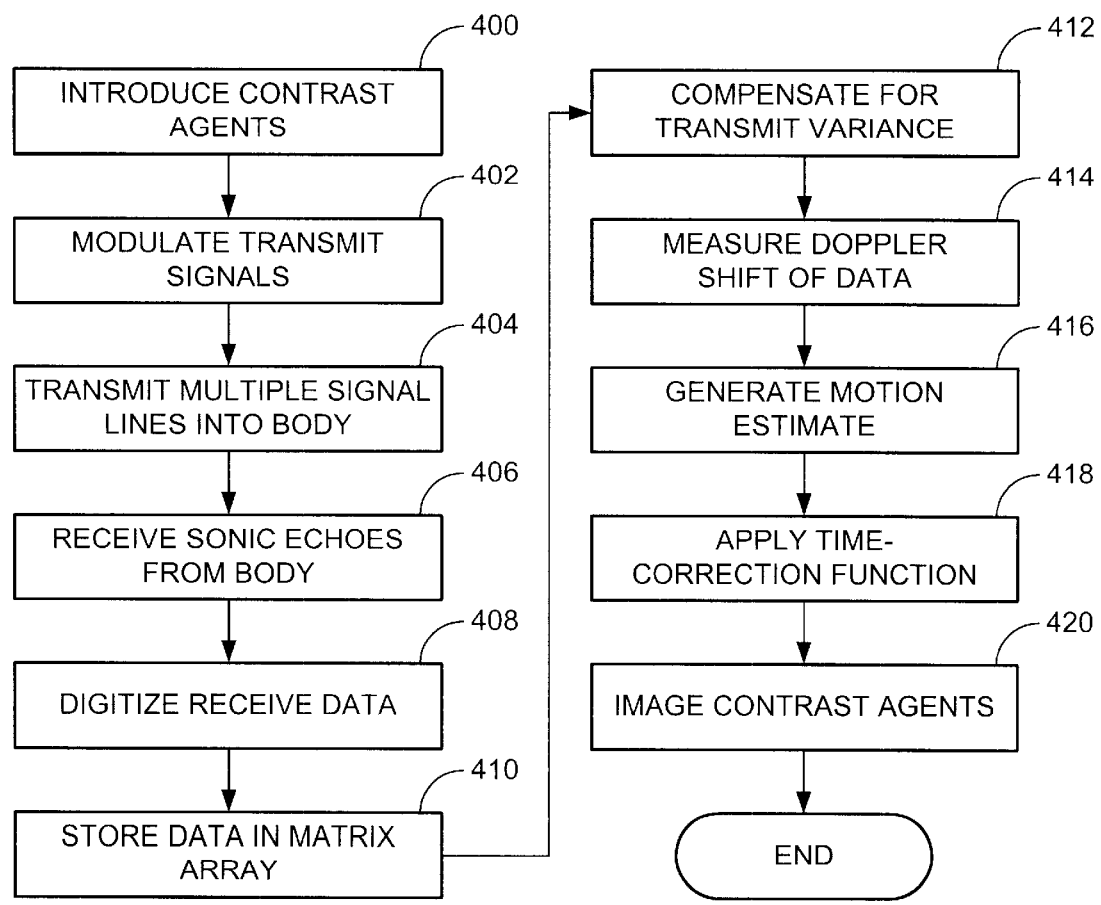
FIG. 4 is a flow diagram of a further method for contrast imaging of the present invention.

A general overview of the imaging method having been provided above, the preferred method will now be discussed in greater detail with reference to FIG. 4. As indicated in this figure, contrast agents are administered to the patient, as indicated in block 400, in similar manner as described above. Prior to ultrasound signals being transmitted into the body, however, the transmit signals are modulated to provide a basis for suppressing linear tissue response as indicated at block 402. This suppression normally comprises exploition of the linearity of the human tissue response and the nonlinearity of the contrast agent response. Because of this distinction, tissue and contrast agents react differently to variations in the transmit signals. In a preferred embodiment, multiple transmit lines having varied transmit characteristics are used. These transmit signals can be modulated through one of several techniques to obtain a variation in the received data.

In a first modulation technique, the amplitude of the transmit signals is varied from transmit line to transmit line to provide power modulation of the transmit signals. For instance, if five separate lines are fired along the same line of sight, the amplitudes of the various lines can be scaled such that the first, third, and fifth lines have an amplitude that is half that of the second and fourth transmitted lines (i.e., 0.5, 1.0, 0.5, 1.0, 0.5). Due to the linear response characteristics of tissue, the tissue response to the half-amplitude transmit signals will be half the magnitude of that of the tissue response to the full amplitude transmit signals. A gain factor can then be applied to the receive data to account for the unequal transmitted amplitudes. For instance, in the transmission scheme described above, the first, third and fifth line responses can be multiplied by a factor of two. When this is done, the response signals of the various transmit lines can be subtracted from each other to cancel all linear components of the signals. Due to the non-linearity of the contrast agent response characteristics, however, this subtraction does not cancel contrast agent signals. Accordingly, through this technique, the stationary tissue signals can be suppressed to improve the signal-to-noise ratio of the data. For a detailed example of power modulation of transmit signals, reference is made to U.S. Pat. No. 5,577,505, issued to Brock-Fisher, et al, commonly assigned with the present application, and which is hereby incorporated by reference into the present disclosure.

Although power modulation provides an effective means for compensating for stationary tissue, other techniques are available. In a second modulation technique, the various transmit signals can be phase modulated. With this technique, the carrier phase of the transmit signals is varied from line to line. By way of example, the phase of the transmit waveform can be incrementally altered by 90° line by line. As with the power modulation technique, this modulation produces variations in the response signals received from the body. The linear components of these response signals will be phase shifted to the same degree as the transmit signals from which they were created. Accordingly, if the receive data is phase adjusted to account for these phase shifts, the linear components of the response data can again be cancelled to suppress the stationary tissue response. For detailed examples of phase modulation, reference is made to U.S. Pat. No. 5,632,277, issued to Chapman, et al. and U.S. Pat. No. 5,902,243, issued to Holley, et al, each of which is hereby incorporated by reference into the present disclosure.

In a third modulation technique, the polarity of the transmit signals is varied. For instance, the various transmit lines can have alternating positive and negative polarities. Again, once the data received from these transmit lines are corrected to account for the variations in the transmit signals, the linear components of the received data can be cancelled to attenuate the response of the stationary tissue. For a detailed example of polarity modulation, reference is made to U.S. Pat. No. 5,706,819, issued to Huang, et al., which is hereby incorporated by reference into the present disclosure.

Irrespective of the particular transmit signal modulation technique used, each transmit line normally comprises repeated sequences of waveforms. By way of example, each waveform comprises a Gaussian-modified sinusoid. The various transmit lines are fired along the same line of sight into the body as indicated in block 404. Each group of lines fired in this direction is referred to as a packet of lines. Normally, specific sequences of transmit waveforms are used and repeated multiple times within each packet. Each sequence of transmit waveforms is referred to as a sub-packet.

Figure 5:
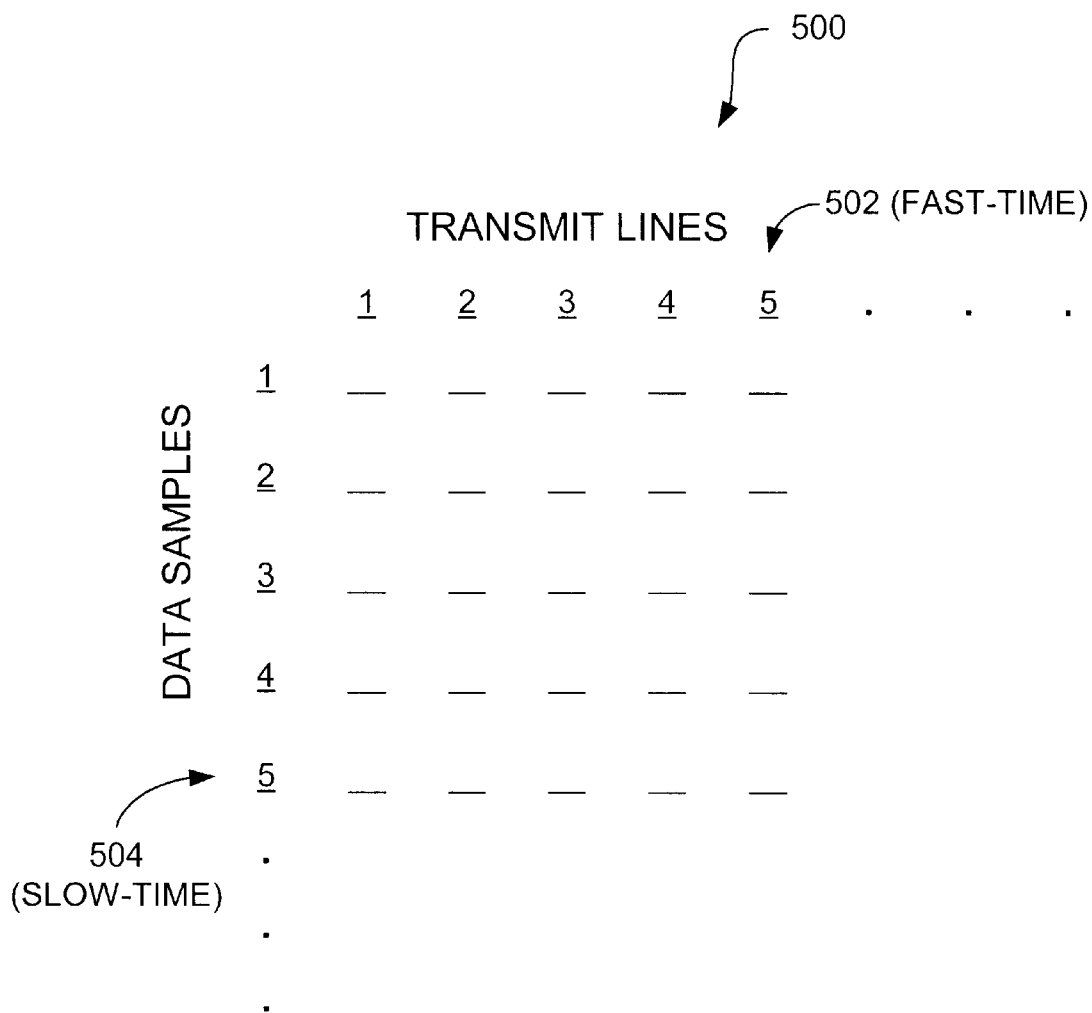
FIG. 5 is a schematic view of a matrix array of received data.

After the multiple lines have been transmitted into the body, the response echoes are received as indicated in block 406. Again, these received signals are digitized, as indicated in block 408, so that the data contained therein can be processed in the appropriate manner. Once digitized, these received data are stored in memory 102 (FIG. 2). Preferably, the data are organized in a matrix array of data points as in block 410. FIG. 5 illustrates an example of such an array 500. In this array 500, there are as many columns 502 as there are lines in the packet. Each column 502 contains a collection of samples which correlate to a particular transmit line. There are as many rows 504 in the array 500 as there are digitized data samples along any one of the received lines. Each successive sample along a row 504 is representative of a particular imaging depth, but acquired a full line-time after the previous sample. Normally, the row 504 direction of the matrix is referred to as slow-time. Each successive data point down each column 502 is acquired immediately after the previous one of the line. Accordingly, the column direction of the matrix normally is referred to as fast-time.

Once the various received data have been stored in the matrix array, the first stage of processing can be conducted. First, a correction function is applied to the data to compensate for the variance of the transmit signals across the multiple lines as indicated in block 412. The nature of the correction function depends upon the particular modulation scheme used to vary the transmit signals. For instance, if the transmit signals were varied according to amplitude (i.e., power modulation), the correction function can comprise a scaling factor which accounts for the amplitude variance across the signal lines. If phase modulation was used in creating the transmit signals, the correction function can comprise a phase adjustment which accounts for the phase variance of the transmit signal. Similarly, where the transmit signals were varied in polarity, the correction can comprise inverting the receive data for the positive or the negative transmit lines.

After the transmit variance has been accounted for in the manner described above, the various lines of data can be subtracted from the other, for instance with a contrast imaging clutter filter, to cancel the linear components of the data. However, before this cancellation is effected, the response of moving tissue is suppressed. As will be understood by persons having ordinary skill in the art, if there is any appreciable motion of tissue between the successive lines of the packets, the received echo data will not cancel precisely, and some residual signal due from moving tissue will remain. Therefore, it is preferable to compensate for this motion before attempting to cancel the linear signals of moving tissue from the received data.

As is known in the art, Doppler flow processing techniques using adaptive clutter filters have been used in the art to compensate for moving tissue in color flow imaging. However, because of the transmit pulse variations used in contrast imaging techniques, conventional adaptive clutter filters used in color flow imaging will not function properly in the contrast imaging scenario. In particular, such filters are captured by the strong transmit variations used in contrast to imaging. In the present invention, however, Doppler flow processing techniques are used in conjunction with contrast imaging techniques to yield clear images of contrast agents without motion artifacts.

The Doppler shift of the transmit variation-compensated received data is first measured as indicated in block 414. From this Doppler shift measurement, an estimate of the tissue motion can be calculated as identified in block 416. Normally, this motion estimate is generated by processing a single row of data from the stored matrix array to derive the motion estimate. As will be appreciated by persons having ordinary skill in the art, the particular algorithm used to derive the estimate can take many forms. For instance, in its simplest form, the estimate can be obtained by deriving the average phase change per slow-time point along the selected row of the matrix array. Alternatively, a multi-valued motion estimate can be obtained by deriving a function of the velocity in terms of slow-time points across the selected row. In another embodiment, an ensemble or subset of the fast-time data from one column can be cross-correlated with a corresponding length ensemble or subset of fast-time data from an adjacent column to generate a motion estimate. In that it is the stronger signals that represent the movement of tissue, each of these processing techniques respond well to tissue signals as opposed to the weaker contrast agent signals.

As will be appreciated by persons having ordinary skill in the art, it may be desirable to enhance the strength of the tissue signals when formulating the motion estimate to maximize cancellation of the moving tissue response. This can be accomplished by, for example, deriving the motion estimate using data received at the fundamental (i.e., transmit) frequency where the tissue response is strongest. By way of example, the digital filter 26 can be centered on the fundamental frequency so as to pass these signals on to the image correction processor 28 (FIG. 1). Once the motion estimate has been generated with the fundamental frequency data, the second harmonic data can be subsequently processed to detect contrast agent concentration or flow.

Once the motion estimate has been generated in the manner described above, this estimate can be used to apply a time-correction function to the successive lines of the original received data as indicated in block 418. By way of example, this time-correction function can be independently applied to ensembles or subsets of points from each column of fast-time data with an all-pass resampling filter. An all-pass resampling filter can be implemented as a finite-impulse-response (FIR) filter, in which the coefficients are chosen to provide a specified time delay in the output as compared to the input. The delay value may be positive or negative. For such a filter of specific length, different coefficients can be calculated to yield a specific desired delay in the data. Typically, the resampling filter uses a plurality of all-pass filter coefficients that can be applied to the data to time-shift the data. For the desired delay value, the required coefficients can be calculated in real-time. Alternatively, in that a reasonable approximation can be had by compensating the delay in quanitized steps, a set of coefficients could be pre-calculated and stored, and the appropriate coefficients selected for use depending on the desired delay. When applied, these coefficients create a localized time delay in the fast-time data that results in a new, time-corrected set of data points. It can also be seen that if the required amount of delay exceeds the fast-time sampling interval, coarse delay correction can be made simply by selecting a different subset or ensemble of data points for input to the FIR resampling filter, which can then be used to apply the remaining residual delay required. As the motion estimate is based independently on each row of slow-time data, it will be understood that f or any packet, the estimate of motion w ill vary with depth as the different tissues being imaged may have different motions at each depth. By processing in this manner, the original receive data can be corrected to de-emphasize tissue motion. For a detailed example of creating a motion estimate and correcting for motion in the color flow imaging context, reference is made to U.S. Pat. No. 5,197,477, issued to Peterson et al., which is hereby incorporated by reference into the present disclosure.

In that the amount of motion from data point to data point can be relatively small, for instance on the order of a fraction of a wavelength per slow-time interval, it may be desirable in some situations to, alternatively, make an assumption as to tissue motion and apply a motion correction factor to the slow-time lines one line at a time instead of applying a correction factor to the entire matrix array at once. Operating in this manner, fewer computations are necessary to correct for motion effects. Using the assumption (i.e., approximation), motion correction can be achieved, for instance, by applying a phase shift either to the original data, or to the coefficients of the contrast imaging clutter filter.

After the effects of the moving tissue signals have been suppressed, the various data can be processed in a second stage to remove the linear components of the data that pertain to tissue as indicated in block 420. As described above, this normally comprises subtracting the various lines of data from each other with a contrast imaging clutter filter to cancel the linear components. By way of example, the data of the first column (line 1) can be subtracted from that of the second column (line 2) to filter the linear components portion of the signal, so that only non-linear components remain.

Once the linear components of the signal have been removed in this manner, the data can be processed to image the contrast agents as indicated in block 422. In one embodiment, this imaging can comprise contrast agent concentration imaging according to known techniques. In another embodiment, techniques similar to those in used color flow imaging can be used to image the direction and velocity of travel of the contrast agents within the bloodstream. In either case, however, advantageous results are obtained due to the suppression of the moving and stationary tissue responses. Although the techniques described herein compensate for the response of moving contrast agents as well as of moving tissue, this compensation is beneficial in that all gross motion is filtered from the data used to image contrast agent concentration. Similarly, beneficial results are obtained where contrast agent velocity is measured in that, once the gross motion has been removed, corrected contrast agent velocities relative to the tissue motion are obtained. This relative velocity of contrast agent to surrounding tissue is of particular clinical significance, especially when imaging moving structures such as the heart.

While particular embodiments of the invention have been disclosed in detail in the foregoing description and drawings for purposes of example, it will be understood by those skilled in the art that variations and modifications thereof can be made without departing from the scope of the invention as set forth in the following claims.

What is claimed is:

1. A method for imaging contrast agents within a patient's body by which motion-related artifacts are reduced, comprising:

receiving echoed signals from the body;

processing the received data to correct for motion effects using a motion estimate representative of tissue and contrast agent motion within the patient's body;

processing the received data to suppress tissue response including time-correcting data received from successive transmit lines using a time-correction function based on said motion estimate; and imaging the contrast agents.

2. The method of claim 1, further comprising transmitting a plurality of signal lines, at least a subset of which are fired along the same direction, into the body.

3. The method of claim 2, further comprising modulating the signal lines in the subset so that they have different transmit characteristics.

4. The method of claim 3, wherein the signal lines in the subset are modulated to have different amplitudes.

5. The method of claim 3, wherein the signal lines in the subset are modulated to have different phases.

6. The method of claim 3, wherein the signal lines in the subset are modulated to have different polarities.

7. The method of claim 2, wherein step of processing the received data to correct for motion effects comprises applying a correction function to the received data to account for variance in the transmitted signal lines.

8. The method of claim 7, wherein the step of processing the received data to correct for motion effects further comprises measuring the Doppler shift of the output of the correction function to generate a motion estimate representative of tissue and contrast agent motion within the body.

9. The method of claim 8, wherein the motion estimate is obtained by deriving the average phase change across the signal lines in the subset at a particular imaging depth.

10. The method of claim 8, wherein the motion estimate is obtained by deriving a velocity function of the phase change across the signal lines in the subset at a particular imagining depth.

11. The method of claim 8, wherein the motion estimate is obtained by cross-correlating data from one signal line in the subset with data from an adjacent signal line in the subset.

12. The method of claim 8, wherein the data used for determining the motion estimate is fundamental frequency data.

13. The method of claim 8, wherein the step of processing the received data to correct for motion effects further comprises applying a time-correct function to the received data based upon the motion estimate.

14. The method of claim 13, wherein the time-correct function comprises a phase adjustment applied to received slow-time data.

15. The method of claim 13, wherein the step of applying a time-correct function comprises applying a phase correction to coefficients of a contrast agent clutter filter.

16. The method of claim 13, wherein the step of applying a time-correct function comprises applying the time-correct function to the received data with an all-pass resampling filter.

17. The method of claim 16, wherein the all-pass resampling filter is a finite-impulse-response filter.

18. The method of claim 2, wherein the processing to suppress stationary tissue response comprises summing signal line data to cancel linear components of the received data.

19. The method of claim 2, wherein the imaging of the contrast agents comprises imaging contrast agent concentration.

20. The method of claim 2, wherein the imaging of the contrast agents comprises imaging contrast agent flow.

21. A system for imaging contrast agents within a patient's body by which motion-related artifacts are reduced, comprising:
    means for receiving echoed signals from the body, and extracting received data therefrom;
    means for processing the received data to correct for motion effects using a motion estimate representative of tissue and contrast agent motion within the patient's body;
    means for processing the received data to suppress tissue response including applying the time-correction function based on said motion estimate; and
    means for imaging the contrast agents.

22. The system of claim 21, further comprising means for transmitting a plurality of signal lines along the same direction.

23. The system of claim 22, further comprising means for modulating the signal lines so that they have different transmit characteristics.

24. The system of claim 22, wherein the means for processing the received data to correct for motion effects comprises means for applying a correction function to the received data to account for variance in the transmitted signal lines.

25. The system of claim 22, wherein the means for processing the received data to correct for motion effects further comprises means for measuring the Doppler shift of the corrected received data to generate a motion estimate representative of tissue and contrast agent motion within the body.

26. The system of claim 25, further comprising means for applying a time-correct function to the received data based upon the motion estimate to correct the data for motion effects.

27. The system of claim 26, wherein the means for applying a time-correct function comprises an all-pass resampling filter.

28. The system of claim 22, wherein the means for processing the received data to suppress stationary tissue response comprises means for summing signal line data to cancel linear components of the data.

29. A system for imaging contrast agents within a patient's body by which motion-related artifacts are reduced, comprising:
    logic configured to receive echoed signals from the body, and extracting received data therefrom;
    logic configured to process the received data to correct for motion effects using a motion estimate representative of tissue and contrast agent motion within the patient's body;
    logic configured to process the received data to suppress tissue response including applying the time-correcting received data using a time-correction function based on said motion estimate; and
    logic configured to image the contrast agents.

30. The system of claim 29, further comprising logic configured to transmit a plurality of signal lines along the same direction.

31. The system of claim 30, further comprising logic configured to modulate the signal lines so that they have different transmit characteristics.

32. The system of claim 30, wherein the logic configured to process the received data to correct for motion effects comprises logic configured to apply a correction function to the received data to account for variance in the transmitted signal lines.

33. The system of claim 30, wherein the logic configured to correct the received data for motion effects further comprises logic configured to measure the Doppler shift of the corrected received data to generate a motion estimate representative of tissue and contrast agent motion within the body.

34. The system of claim 33, further comprising logic configured to apply a time-correct function to the received data based upon the motion estimate to correct the data for motion effects.

35. The system of claim 34, wherein the logic configured to apply a time-correct function comprises an all-pass resampling filter.

36. The system of claim 30, wherein the logic configured to process the received data to suppress stationary tissue response comprises logic configured to sum signal line data to cancel linear components of the data.

* * * * *